(12) United States Patent
Knobloch et al.

(10) Patent No.: US 12,310,741 B2
(45) Date of Patent: May 27, 2025

(54) GENERATION OF MRI IMAGES OF THE LIVER

(71) Applicant: BAYER AKTIENGESELLSCHAFT, Leverkusen (DE)

(72) Inventors: Gesine Knobloch, Berlin (DE); Christian Lienerth, Frankfurt am Main (DE)

(73) Assignee: BAYER AKTIENGESELLSCHAFT, Leverkusen (DE)

(*) Notice: Subject to any disclaimer, the term of this patent is extended or adjusted under 35 U.S.C. 154(b) by 487 days.

(21) Appl. No.: 17/655,017

(22) PCT Filed: Sep. 10, 2020

(86) PCT No.: PCT/EP2020/075288
§ 371 (c)(1),
(2) Date: Mar. 16, 2022

(87) PCT Pub. No.: WO2021/052850
PCT Pub. Date: Mar. 25, 2021

(65) Prior Publication Data
US 2023/0218223 A1    Jul. 13, 2023

(30) Foreign Application Priority Data
Sep. 18, 2019    (EP) .................................... 19197986

(51) Int. Cl.
*A61B 5/00*    (2006.01)
*A61B 5/055*    (2006.01)
*G06T 7/00*    (2017.01)

(52) U.S. Cl.
CPC ............ *A61B 5/4244* (2013.01); *A61B 5/055* (2013.01); *G06T 7/0012* (2013.01); *G06T 2207/10088* (2013.01)

(58) Field of Classification Search
CPC ..... A61B 5/4244; A61B 5/055; G06T 7/0012; G06T 2207/10088
USPC ......................................................... 382/128
See application file for complete search history.

(56) References Cited

U.S. PATENT DOCUMENTS

| | | |
|---|---|---|
| 732,697 A | 7/1903 | Bates |
| 5,732,697 A | 3/1998 | Zhang et al. |
| 5,840,026 A | 11/1998 | Uber, III et al. |
| 6,039,931 A | 3/2000 | Schmitt-Willich et al. |
| 6,643,537 B1 | 11/2003 | Zatezalo et al. |
| 6,754,376 B1 | 6/2004 | Turek et al. |
| 6,819,790 B2 | 11/2004 | Suzuki et al. |

(Continued)

FOREIGN PATENT DOCUMENTS

| | | |
|---|---|---|
| CN | 104769641 A | 7/2015 |
| CN | 107492090 A | 12/2017 |

(Continued)

OTHER PUBLICATIONS

Bannas; et al, "Combined Gadoxetic Acid and Gadofosveset Enhanced Liver MRI: A Feasibility and Parameter Optimization Study", Magnetic Resonance in Medicine, 2016, 75, 318-328.

(Continued)

*Primary Examiner* — Michael R Neff
(74) *Attorney, Agent, or Firm* — Ann H. Inglett

(57) ABSTRACT

The present invention relates to the generation of artificial MRI images of the liver. The invention also relates to a method, a system and a computer program product for generating MRI images of the liver.

17 Claims, 7 Drawing Sheets

(56) References Cited

U.S. PATENT DOCUMENTS

| | | |
|---|---|---|
| 7,564,990 B2 | 7/2009 | Kern et al. |
| 7,738,683 B2 | 6/2010 | Cahill et al. |
| 7,937,134 B2 | 5/2011 | Uber et al. |
| 7,949,167 B2 | 5/2011 | Krishnan et al. |
| 8,060,178 B2 | 11/2011 | Zhou et al. |
| 8,155,406 B2 | 4/2012 | Mattiuzzi |
| 9,311,702 B2 | 4/2016 | Pautot |
| 9,449,381 B2 | 9/2016 | Liang |
| 9,616,166 B2 | 4/2017 | Kalafut et al. |
| 9,754,371 B2 | 9/2017 | Kateb et al. |
| 9,959,615 B2 | 5/2018 | Liang et al. |
| 10,157,467 B2 | 12/2018 | Dincer et al. |
| 10,176,408 B2 | 1/2019 | Paik et al. |
| 10,335,106 B2 | 7/2019 | Kim |
| 10,555,773 B2 | 2/2020 | Higaki et al. |
| 10,634,753 B2 | 4/2020 | De Weerdt |
| 10,645,359 B2 | 5/2020 | Bist et al. |
| 10,933,186 B2 | 3/2021 | Uber, III |
| 11,246,558 B2 | 2/2022 | Uber, III et al. |
| 11,308,613 B2 | 4/2022 | Chitiboi et al. |
| 2005/0100208 A1 | 5/2005 | Suzuki et al. |
| 2006/0018524 A1 | 1/2006 | Suzuki et al. |
| 2007/0047787 A1 | 3/2007 | Oakley et al. |
| 2008/0317315 A1 | 12/2008 | Stemmer |
| 2010/0198054 A1 | 8/2010 | Ewing et al. |
| 2011/0029248 A1 | 2/2011 | Saeed et al. |
| 2013/0035921 A1 | 2/2013 | Rodriguez-Ponce et al. |
| 2013/0297554 A1 | 11/2013 | Mah |
| 2014/0062481 A1 | 3/2014 | Greiser et al. |
| 2014/0257854 A1 | 9/2014 | Becker et al. |
| 2015/0125398 A1 | 5/2015 | Assouline et al. |
| 2016/0000945 A1 | 1/2016 | Nedergaard et al. |
| 2016/0035093 A1 | 2/2016 | Kateb et al. |
| 2016/0038092 A1 | 2/2016 | Golay |
| 2016/0109539 A1 | 4/2016 | Mardor et al. |
| 2017/0243349 A1 | 8/2017 | Hou et al. |
| 2017/0245817 A1 | 8/2017 | Berlin et al. |
| 2017/0269182 A1 | 9/2017 | Beck |
| 2017/0281278 A1 | 10/2017 | Higaki et al. |
| 2018/0242917 A1 | 8/2018 | Bagherzadeh et al. |
| 2018/0315183 A1 | 11/2018 | Milioni De Carvalho et al. |
| 2019/0012932 A1 | 1/2019 | Higaki et al. |
| 2019/0099145 A1 | 4/2019 | Kim |
| 2019/0122348 A1 | 4/2019 | Jensen |
| 2019/0310338 A1 | 10/2019 | James et al. |
| 2019/0317171 A1 | 10/2019 | Nayak et al. |
| 2019/0318474 A1 | 10/2019 | Han |
| 2019/0362522 A1 | 11/2019 | Han |
| 2019/0365340 A1 | 12/2019 | Hao et al. |
| 2020/0167911 A1 | 5/2020 | Park et al. |
| 2020/0202557 A1 | 6/2020 | Schmidt |
| 2020/0242744 A1 | 7/2020 | Schafer et al. |
| 2020/0258629 A1 | 8/2020 | Ahmad et al. |
| 2020/0311932 A1 | 10/2020 | Hooper et al. |
| 2020/0371182 A1 | 11/2020 | Grimm et al. |
| 2021/0012486 A1 | 1/2021 | Huang et al. |
| 2021/0027436 A1 | 1/2021 | Banerjee et al. |
| 2021/0027502 A1 | 1/2021 | Abumoussa et al. |
| 2021/0056734 A1 | 2/2021 | Han |
| 2021/0386389 A1 | 12/2021 | Freiman et al. |
| 2022/0018924 A1 | 1/2022 | Bai et al. |
| 2022/0031270 A1 | 2/2022 | Cohen et al. |
| 2022/0105265 A1 | 4/2022 | Cowan et al. |
| 2022/0351369 A1 | 11/2022 | Haase et al. |

FOREIGN PATENT DOCUMENTS

| | | |
|---|---|---|
| CN | 108324244 A | 7/2018 |
| CN | 109983474 A | 7/2019 |
| EP | 1941460 A1 | 7/2008 |
| EP | 2626718 A1 | 8/2013 |
| EP | 2750102 A1 | 7/2014 |
| EP | 3118644 A1 | 1/2017 |
| EP | 3322997 A1 | 5/2018 |
| EP | 1941460 B1 | 12/2018 |
| EP | 3619631 A1 | 3/2020 |
| EP | 3804615 A1 | 4/2021 |
| EP | 3875979 A1 | 9/2021 |
| JP | 5878009 B2 | 3/2016 |
| KR | 102001398 B1 | 7/2019 |
| WO | 2007053676 A2 | 5/2007 |
| WO | 2009135923 A1 | 11/2009 |
| WO | 2012075577 A1 | 6/2012 |
| WO | 2013121374 A2 | 8/2013 |
| WO | 2014162273 A1 | 10/2014 |
| WO | 2016007734 A1 | 1/2016 |
| WO | 2017040152 A1 | 3/2017 |
| WO | 2017139110 A1 | 8/2017 |
| WO | 2018046412 A1 | 3/2018 |
| WO | 2018183044 A1 | 10/2018 |
| WO | 2018200493 A1 | 11/2018 |
| WO | 2018202541 A1 | 11/2018 |
| WO | 2019046299 A1 | 3/2019 |
| WO | 2019063520 A1 | 4/2019 |
| WO | 2019074938 A1 | 4/2019 |
| WO | 2019102846 A1 | 5/2019 |
| WO | 2019204406 A1 | 10/2019 |
| WO | 2019241659 A1 | 12/2019 |
| WO | 2021052850 A1 | 3/2021 |
| WO | 2021069338 A1 | 4/2021 |
| WO | 2021069343 A1 | 4/2021 |
| WO | 2021197996 A1 | 10/2021 |

OTHER PUBLICATIONS

Cannella; et al, "Common pitfalls when using the Liver Imaging Reporting and Data System (LI-RADS): lessons learned from a multi-year experience", Abdominal Imaging, Aug. 2, 2018, 43-53.

Caraiani; et al, "Description of Focal Liver Lesions With GD-EOB-DTPA Enhanced MRI", Clujul Medical, 2015, vol. 88 No. 4, 438-448.

Conversano; et al, "Hepatic Vessel Segmentation for 3D Planning of Liver Surgery: Experimental Evaluation of a New Fully Automatic Algorithm", Academic Radiology, Apr. 2011, vol. 18/ No. 4, 461-470.

Fischer; et al, "Ultra-high-field imaging of the biliary tract of 7 Tesla: initial results of Gd-EOB-DTPA-enhanced MRCP", Proc. Intl. Soc. Mag. Reson. Med., 2012, 20.

Frydrychowicz; et al, "Hepatobiliary MR Imaging with Gadolinium Based Contrast Agents", J Magn Reson Imaging, Mar. 2012, 35 (3), 492-511.

Hope; et al, "Improvement of Gadoxetate Arterial Phase Capture With a High Spatio-Temporal Resolution Multiphase Three-Dimensional SPGR-Dixon Sequence", Journal of Magnetic Resonance Imaging, 2013, 38, 938-945.

"International Preliminary Report on Patentability from PCT Application No. PCT/EP2020/075288", Mar. 31, 2022.

Kim; et al, "Arterial subtraction images of gadoxetate-enhanced MRI improve diagnosis of early-stage hepatocellular carcinoma", Journal of Hepatology, 2019, vol. 71, 534-542.

Kim; et al, "Gadoxetic acid-enhanced magnetic resonance imaging: Hepatocellular carcinoma and mimickers", Clinical and Molecular Hepatology, Sep. 2019, vol. 25 No. 3, 223-233.

Knobloch; et al, "Combined Gadoxetic Acid and Gadobenate Dimeglumine Enhanced Liver MRI for Liver Metastasis Detection: A Parameter Optimization Study", Proc. Intl. Soc. Mag. Reson. Med., 2018.

Marcan; et al, "Segmentation of hepatic vessels from MRI images for planning of electroporation-based treatments In the liver", Radiol. Oncol., 2014, 48 (3), 267-281.

Moccia; et al, "Blood vessel segmentation algorithms—Review of methods, datasets and evaluation metrics", Computer Methods and Programs in Biomedicine, 2018, 158, 71-91.

Yasaka, et al., "Liver Fibrosis: Deep Convolutional Neural Network for Staging by Using Gadoxetic Acid-enhanced Hepatobiliary Phase MR Images", Dec. 14, 2017, Radiology, vol. 287, No. 1.

He, et al., "Deep Predictive Modeling of Dynamic Contrast-Enhanced MRI Data", Proc. Intl. Soc. Mag. Reson. Med., 2019, vol. 27.

(56) References Cited

OTHER PUBLICATIONS

Kurozumi, et al., "Evaluation of hemodynamic imaging findings of hypervascular hepatocellular carcinoma: comparison between dynamic contrast-enhanced magnetic resonance imaging using radial volumetric imaging breath-hold examination with k-space-weighted image contrast reconstruction and dynamic computed tomography during hepatic arteriography", Japanese Journal of Radiology, 2018, pp. 295-302, vol. 36.

Zhang, et al., "Dynamic contrast enhanced MR imaging for evaluation of angiogenesis of hepatocellular nodules in liver cirrhosis in N-nitrosodiethylamine induced rat model", Eur. Radiol., 2017, pp. 2086-2094, vol. 27.

Baccouche; et al, "Sequential Deep Learning for Human Action Recognition", International Workshop on Human Behavior Understanding, 2011, 29-39.

Baytas Inci M.; et al, "Patient Subtyping via Time-Aware LSTM Networks", 2017.

Chiusano; et al, "DCE-MRI Analysis Using Sparse Adaptive Representations", 2011, 67-74.

Coulden; Richard, "State-of-the-Art Imaging Techniques in Chronic Thromboembolic Pulmonary Hypertension", Proceedings of the American Thoracic Society, 2006, vol. 3, 577-583.

Delcroix Marion; et al, "Chronic Thromboembolic Pulmonary Hypertension; Epidemiology and Risk Factors", Annals of the American Thoracic Society, Jul. 2016, vol. 13 Supp. 13, S201-S206.

"FDA Reclassification Letter regarding OsteoDetect", May 24, 2018.

Galie Nazzareno; et al, "2015 ESC/ERS Guidelines for the diagnosis and treatment of pulmonary hypertension", European Heart Journal, Jan. 2016, vol. 37, Issue 1, 67-119.

Ghodasara; Satyam et al, "Quantifying Perfusion Properties with DCE-MRI Using a Dictionary Matching Approach", International Society For Magnetic Resonance In Medicine, ISMRM,, Jun. 1, 2018.

Hachulla; et al, "Dual-energy computed tomographic imaging of pulmonary hypertension", Swiss Medical Weekly, 2016, 146; w14328, 1-20.

Huang Gao.; et al, "Densely Connected Convolutional Networks", Jan. 28, 2018.

"International Preliminary Report on Patentability from PCT Application No. PCT/EP2020/075593", Mar. 31, 2022.

"International Preliminary Report on Patentability from PCT Application No. PCT/EP2020/077775", Apr. 12, 2022.

"International Preliminary Report on Patentability from PCT Application No. PCT/IB2020/058688", Mar. 31, 2022.

"International Preliminary Report on Patentability from PCT Application No. PCT/US2020/021861", Sep. 23, 2021.

"International Search Report and Written Opinion from PCT Application No. PCT/IB2020/058688", Dec. 9, 2020.

Ji; et al, "3D Convolutional Neural Networks for Human Action Recognition", IEEE Transactions on Pattern Analysis and Machine Intelligence, Jan. 2013, vol. 35 No. 1, 221-231.

Karpathy; et al, "Large-scale Video Classification with Convolutional Neural Networks", Proceedings of the IEEE Conference on Computer Vision and Pattern Recognition, 2014, 1725-1732.

Khan; et al, "Chapter 3.3 "Neural Networks Basics"", A Guide to Convolutional Neural Networks for Computer Vision, Morgan & Claypool Publishers, 2018, pp. 36-39.

Kwon; et al, "Differentiation of small (less than or equal to cm) hepatocellular carcinomas from small benign nodules In cirrhotic liver on gadoxetic acid-enhanced and diffusion-weighted magnetic resonance images", Abdominal Imaging, Jul. 6, 2014, pp. 64-78.

Le; Quoc V., "A Tutorial on Deep Learning Part 2: Autoencoders, Convolutional Neural Networks and Recurrent Neural Networks", Oct. 20, 2015.

Meng Qinxue; et al, "Relational Autoencoder for Feature Extraction", Feb. 9, 2018.

Shtern; Alon, "Shape Correspondence Using Spectral Methods and Deep Learning Research Thesis", Aug. 2017.

Simonyan; et al, "Two-Stream Convolutional Networks for Action Recognition in Videos", Advances in Neural Information Processing Systems, 2013, 568-576.

Smith; Dana, "Artificial Intelligence Can Detect Alzheimer's Disease in Braine Scans Six Years Before a Diagnosis", Jan. 2, 2019.

Tapson Victor; et al, "Incidence and Prevalence of Chronic Thromboembolic Pulmonary Hypertension", Proceedings of the American Thoracic Society, Sep. 7, 2006, vol. 3, 564-567.

Thompson; et al, "Indicator Transit Time Considered as a Gamma Variate", Circulation Research, Jun. 1964, vol. XIV, 502-515.

Wang; et al, "Stacked Fully Convolutional Networks for Pulmonary Vessel Segmentation", IEEE Visual Communications and Image Processing (VCIP), 2018.

Weizman; et al, "Prediction of Brain MR Scans in Longitudinal Tumor Follow-Up Studies", Oct. 1, 2012, pp. 179-187.

Bellani; Giacomo et al, "Epidemiology, Patterns of Care, and Mortality for Patients With Acute Respiratory Distress Syndrome in Intensive Care Unites in 50 Countries", JAMA, 2016.

Choi; Jun-Ho et al, "EmbraceNet: A robust deep learning architecture for multimodal classification", Information Fusion, 2019, 51, 259-270.

Gong Enhao; et al, "Deep Learning Enables Reduced Gadolinium Dose for Contrast-Enhanced Brain MRI", J. Magn. Reson. Imaging, 2018, 48, 330-340.

"Information on Primovist", 2016.

"International Preliminary Report on Patentability from PCT Application No. PCT/EP2020/077767", Apr. 12, 2022.

"Introduction to Multimodal Learning Model", DEV Community, Feb. 5, 2019.

Rajpurkar; Pranav et al, "CheXNet: Radiologist-Level Pneumonia Detection on Chest X-Rays with Deep earning", 2017.

Yasaka Koichiro; et al, "Deep Learning with Convolutional Neural Network for Differentiation of Liver Masses at Dynamic Contrast-enhanced CT: A Preliminary Study", Radiology, Mar. 2018, vol. 286; No. 3, 887-896.

Chibuzo; Abonyi et al, "Intravascular Contrast Media in Radiography: Historical Development & Review of Risk Factors for Adverse Reactions", South American Journal of Clinical Research, 2016, Vo. 3, Issue 1.

Ignee; Andre et al, "Ultrasound contrast agents", Endoscopic Ultrasound, Nov.-Dec. 2016, vol. 5, Issue 6, 355-362.

Karani Neerav et al: "Temporal Interpolation of Abdominal MRIs Acquired During Free-Breathing", Sep. 4, 2017 (Sep. 4, 2017), 12th European Conference on Computer Vision, ECCV 2012; [Lecture Notes in Computer Science], Springer Berlin Heidelberg, Berlin, Heidelberg, pp. 359-367, XP047528114, ISSN: 0302-9743 ISBN: 978-3-642-39453-9.

Lusic Hrvoje; et al, "X-Ray Computed Tomography Contrast Agents", Chem. Rev., 2013.

Nouh Mohamed; et al, "Radiographic and magnetic resonances contrast agents: Essentials and tips for safe practices", World Journal of Radiology, Sep. 28, 2017, vol. 9, Issue 9, 339-349.

Qin Chen et al: "Convolutional Recurrent Neural Networks for Dynamic MR Image Reconstruction", IEEE Transactions on Medical Imaging, IEEE Service Center, Piscataway, NJ, US, Bd. 38, Nr. 1, Jan. 1, 2019 (Jan. 1, 2019), Seiten 280-290, P011694961, ISSN: 0278-0062, DOI: 10.1109/TMI.2018.2863670.

Smits Loek; et al, "Evaluation of ultrasmall superparamagnetic iron oxide (USPIO) enhanced MRI with ferumoxytol to quantify arterial wall inflammation", Atherosclerosis, 2017, 263, 211-218.

Takeshima, Hidenori: "Integrating Spatial and Temporal Correlations into a Deep Neural Network for Low-delay Reconstruction of Highly Undersampled Radial Dynamic Images", International Society for Magnetic Resonance in Medicine, ISMRM, 2030 Addison Street, 7th Floor, Berkeley, CA 94704 USA, pp. 2796, Jun. 1, 2018 (Jun. 1, 2018).

"Written Opinion from PCT Application No. PCT/EP2021/057689", Jun. 24, 2021.

XIAO; Yu-Dong et al, "MRI contrast agents: Classification and application (Review)", International Journal of Molecular Medicine, 2016, 38, 1319-1326.

GENERATION OF MRI IMAGES OF THE LIVER

CROSS REFERENCE TO RELATED APPLICATIONS

The present application is a U.S. national stage filing under 35 U.S.C. § 371 of International Application No. PCT/EP2020/075288, filed 10 Sep. 2020, which claims priority to European Patent Application No. EP 19197986.3, filed 18 Sep. 2019, the disclosures of each of which are incorporated in their entirety herein by this reference.

The present disclosure deals with the generation of artificial MRI images of the liver. Subjects of the present disclosure are a method, a system and a computer program product for generating MRI images of the liver.

Magnetic resonance imaging, MRI for short, is an imaging method which is used especially in medical diagnostics for depicting structure and function of the tissue and organs in the human or animal body.

In MRI, the magnetic moments of protons in an examination object are aligned in a basic magnetic field, with the result that there is a macroscopic magnetization along a longitudinal direction. This is subsequently deflected from the resting position by the incident radiation of high-frequency (HF) pulses (excitation). The return of the excited states into the resting position (relaxation) or the magnetization dynamics is subsequently detected by means of one or more HF receiver coils as relaxation signals.

For spatial encoding, rapidly switched magnetic gradient fields are superimposed on the basic magnetic field. The captured relaxation signals or the detected and spatially resolved MRI data are initially present as raw data in a spatial frequency space, and can be transformed by subsequent Fourier transformation into the real space (image space).

In the case of native MRI, the tissue contrasts are generated by the different relaxation times (T1 and T2) and the proton density.

T1 relaxation describes the transition of the longitudinal magnetization into its equilibrium state, T1 being that time that is required to reach 63.21% of the equilibrium magnetization prior to the resonance excitation. It is also called longitudinal relaxation time or spin-lattice relaxation time.

Analogously, T2 relaxation describes the transition of the transversal magnetization into its equilibrium state.

MRI contrast agents develop their action by altering the relaxation times of the structures which take up contrast agents. A distinction can be made between two groups of substances: paramagnetic and superparamagnetic substances. Both groups of substances have unpaired electrons which induce a magnetic field around the individual atoms or molecules.

Superparamagnetic contrast agents lead to a predominant shortening of T2, whereas paramagnetic contrast agents mainly lead to a shortening of T1. A shortening of the T1 time leads to an increase in the signal intensity, and a shortening of the T2 time leads to a decrease in the signal intensity.

The action of said contrast agents is indirect, since the contrast agent itself does not give off a signal, but instead only influences the signal intensity in its surroundings.

In T1-weighted images, the paramagnetic contrast agents lead to a lighter (higher-signal) depiction of the regions containing contrast agent compared to the regions containing no contrast agent.

In T2-weighted images, superparamagnetic contrast agents lead to a darker (lower-signal) depiction of the regions containing contrast agent compared to the regions containing no contrast agent.

Both a higher-signal depiction and a lower-signal depiction lead to a contrast enhancement.

An example of a superparamagnetic contrast agent are iron oxide nanoparticles (SPIO: superparamagnetic iron oxide).

Examples of paramagnetic contrast agents are gadolinium chelates such as gadopentetate dimeglumine (trade name: Magnevist® and others), gadobenate dimeglumine (trade name: Multihance®), gadoteric acid (Dotarem®, Dotagita®, Cyclolux®), gadodiamide (Omniscan®), gadoteridol (ProHance®) and gadobutrol (Gadovist®).

Extracellular, intracellular and intravascular contrast agents can be distinguished according to their pattern of spreading in the tissue.

Contrast agents based on gadoxetic acid are characterized by specific uptake by liver cells, the hepatocytes, by enrichment in the functional tissue (parenchyma) and by enhancement of the contrasts in healthy liver tissue. The cells of cysts, metastases and most liver-cell carcinomas no longer function like normal liver cells, do not take up the contrast agent or hardly take it up, are not depicted with enhancement, and are identifiable and localizable as a result.

Examples of contrast agents based on gadoxetic acid are described in U.S. Pat. No. 6,039,931A; they are commercially available under the trade names Primovist® or Eovist® for example.

The contrast-enhancing effect of Primovist®/Eovist® is mediated by the stable gadolinium complex Gd-EOB-DTPA (gadolinium ethoxybenzyl diethylenetriamine pentaacetic acid). DTPA forms, with the paramagnetic gadolinium ion, a complex which has an extremely high thermodynamic stability. The ethoxybenzyl (EOB) radical is the mediator of the hepatobiliary uptake of the contrast agent.

Primovist® can be used for the detection of tumours in the liver. Blood supply to the healthy liver tissue is primarily achieved via the portal vein (vena portae), whereas the liver artery (arteria hepatica) supplies most primary tumours. After intravenous injection of a bolus of contrast agent, it is accordingly possible to observe a time delay between the signal rise of the healthy liver parenchyma and of the tumour.

In the case of the contrast enhancement achieved by Primovist® during the distribution phase, what are observed are typical perfusion patterns which provide information for the characterization of the lesions. Depicting the vascularization helps to characterize the lesion types and to determine the spatial relationship between tumour and blood vessels.

In the case of T1-weighted images, Primovist® leads, 10-20 minutes after the injection (in the hepatobiliary phase), to a distinct signal enhancement in the healthy liver parenchyma, whereas lesions containing no hepatocytes or only a few hepatocytes, for example metastases or moderately to poorly differentiated hepatocellular carcinomas (HCCs), appear as darker regions.

However, the blood vessels also appear as dark regions in the hepatobiliary phase, meaning that, in the MRI images which are generated during the hepatobiliary phase, it is not possible to differentiate liver lesions and blood vessels solely on the basis of the contrast. A differentiation between liver lesions and blood vessels can only be achieved in connection with images in the dynamic phase in which the blood vessels are highlighted. Thus, when looking at MRI images which were generated during the dynamic phase, the radiologist must note the blood vessels in order to be able to distinguish them from liver lesions in MRI images which were generated during the hepatobiliary phase.

The present disclosure attends to this problem with the subjects of the independent claims. Preferred embodiments of the present disclosure are found in the dependent claims, in this description and in the drawings.

Figure 1:
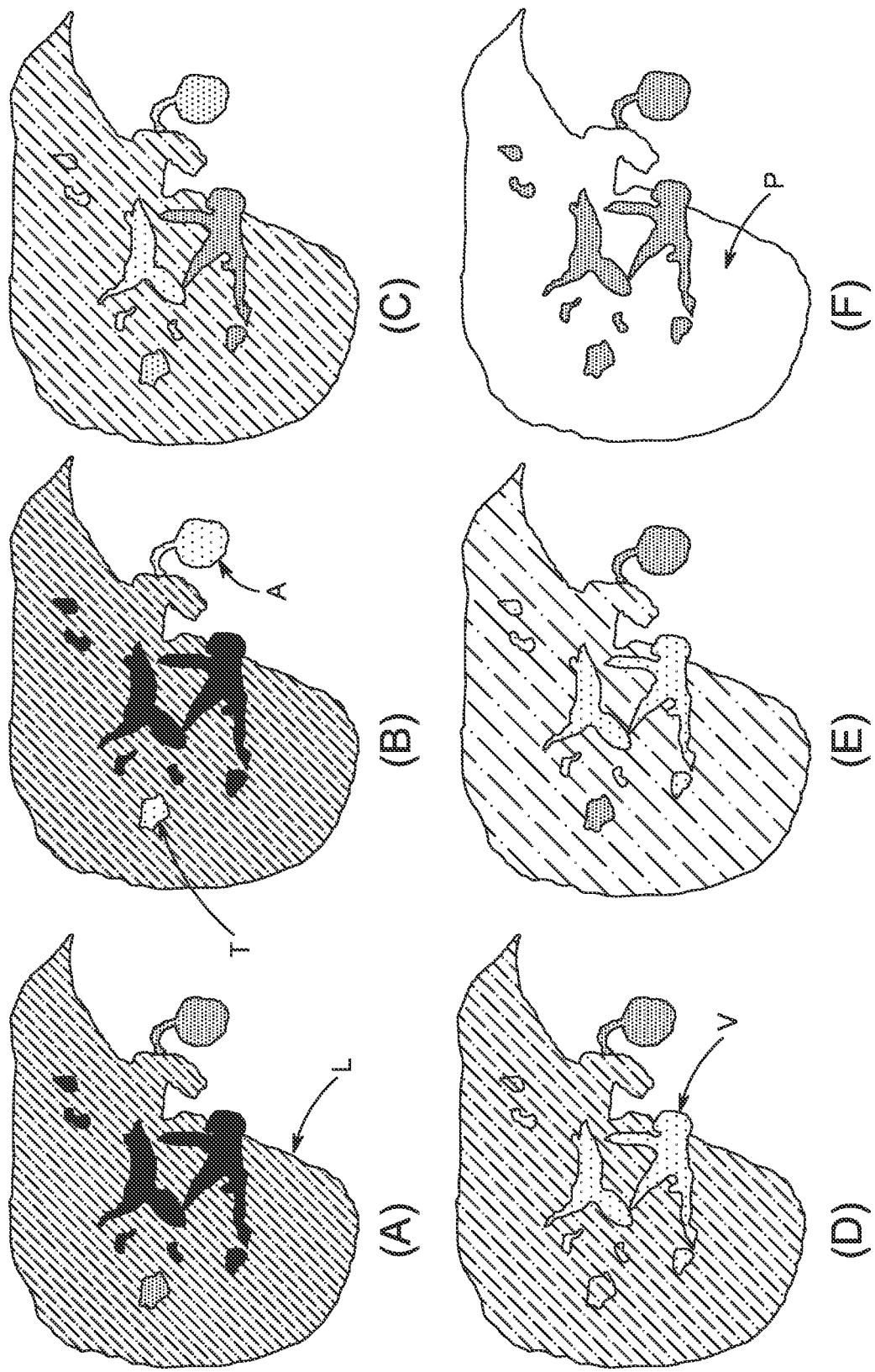
FIG. 1 schematically shows MRI images of a liver during a dynamic phase and hepatobiliary phase.

The present disclosure provides, in a first aspect, a method comprising the steps of:
receiving at least one first MRI image of an examination object, the at least one first MRI image showing a liver or a portion of a liver of the examination object, blood vessels in the liver being depicted with contrast enhancement as a result of a contrast agent,
receiving at least one second MRI image of the same examination object, the at least one second MRI image showing the same liver or the same portion of the liver, healthy liver cells being depicted with contrast enhancement as a result of a contrast agent,
generating at least one third MRI image by combining the at least one first MRI image with the at least one second MRI image and leveling out the difference in contrast between blood vessels and healthy liver cells,
displaying and/or outputting the at least one third MRI image and/or storing the at least one third MRI image in a data storage medium.

The present disclosure further provides a system comprising:
a receiving unit,
a control and calculation unit, and
an output unit,
the control and calculation unit being configured to prompt the receiving unit to receive at least one first MRI image of an examination object, the at least one first MRI image showing a liver or a portion of a liver of the examination object, blood vessels in the liver being depicted with contrast enhancement as a result of a contrast agent,
the control and calculation unit being configured to prompt the receiving unit to receive at least one second MRI image of an examination object, the at least one second MRI image showing the same liver or the same portion of the liver, healthy liver cells being depicted with contrast enhancement as a result of a contrast agent,
the control and calculation unit being configured to generate at least one third MRI image by combining the at least one first MRI image and the at least one second MRI image and leveling out the difference in contrast between blood vessels and healthy liver cells,
the control and calculation unit being configured to prompt the output unit to display the at least one third MRI image, to output it or to store it in a data storage medium.

The present disclosure further provides a computer program product comprising a computer program which can be loaded into a memory of a computer system, where it prompts the computer system to execute the following steps:
receiving at least one first MRI image of an examination object, the at least one first MRI image showing a liver or a portion of a liver of the examination object, blood vessels in the liver being depicted with contrast enhancement as a result of a contrast agent,
receiving at least one second MRI image of the same examination object, the at least one second MRI image showing the same liver or the same portion of the liver, healthy liver cells being depicted with contrast enhancement as a result of a contrast agent,
generating at least one third MRI image by combining the at least one first MRI image with the at least one second MRI image and leveling out the difference in contrast between blood vessels and healthy liver cells,
displaying and/or outputting the at least one third MRI image and/or storing the at least one third MRI image in a data storage medium.

The present disclosure further provides for the use of a contrast agent in an MRI method, the MRI method comprising the following steps:
administering the contrast agent, the contrast agent spreading in a liver of an examination object,
generating at least one first MRI image, the at least one first MRI image showing the liver or a portion of the liver of the examination object, blood vessels in the liver being depicted with contrast enhancement as a result of the contrast agent,
generating at least one second MRI image, the at least one second MRI image showing the same liver or the same portion of the liver, healthy liver cells being depicted with contrast enhancement as a result of the contrast agent,
generating at least one third MRI image by combining the at least one first MRI image with the at least one second MRI image and leveling out the difference in contrast between blood vessels and healthy liver cells,
displaying and/or outputting the at least one third MRI image and/or storing the at least one third MRI image in a data storage medium.

Further provided is a contrast agent for use in an MRI method, the MRI method comprising the following steps:
administering the contrast agent, the contrast agent spreading in a liver of an examination object,
generating at least one first MRI image, the at least one first MRI image showing the liver or a portion of the liver of the examination object, blood vessels in the liver being depicted with contrast enhancement as a result of the contrast agent,
generating at least one second MRI image, the at least one second MRI image showing the same liver or the same portion of the liver, healthy liver cells being depicted with contrast enhancement as a result of the contrast agent, generating at least one third MRI image by combining the at least one first MRI image with the at least one second MRI image and leveling out the difference in contrast between blood vessels and healthy liver cells, displaying and/or outputting the at least one third MRI image and/or storing the at least one third MRI image in a data storage medium.

Further provided is a kit comprising a contrast agent and a computer program product according to the disclosure.

The disclosure will be more particularly elucidated below without distinguishing between the subjects of the disclosure (method, system, computer program product, use, contrast agent for use, kit). On the contrary, the following elucidations are intended to apply analogously to all the subjects of the disclosure, irrespective of in which context (method, system, computer program product, use, contrast agent for use, kit) they occur.

If steps are stated in an order in the present description or in the claims, this does not necessarily mean that the disclosure is restricted to the stated order. On the contrary, it is conceivable that the steps are also executed in a different order or else in parallel to one another, unless one step builds upon another step, this absolutely requiring that the building step be executed subsequently (this being, however, clear in the individual case). The stated orders are thus preferred embodiments of the disclosure.

The present disclosure generates artificial MRI images of a liver or of a portion of a liver of an examination object, in which the contrast between the blood vessels in the liver and the liver cells is artificially minimized in order to make liver lesions more easily identifiable.

The "examination object" is usually a living being, preferably a mammal, very particularly preferably a human.

A portion of the examination object is subjected to a contrast-enhanced magnetic resonance imaging examination. The "examination region", also called image volume (field of view, FOV), is in particular a volume which is imaged in the magnetic resonance images. The examination region is typically defined by a radiologist, for example on an overview image (localizer). It is self-evident that the examination region can, alternatively or additionally, also be defined automatically, for example on the basis of a selected protocol. The examination region comprises at least one portion of the liver of the examination object.

The examination region is introduced into a basic magnetic field.

A contrast agent which spreads in the examination region is administered to the examination object. The contrast agent is preferably administered intravenously as a bolus (e.g. into a vein in the arm).

A "contrast agent" is understood to mean a substance or substance mixture, the presence of which in a magnetic resonance measurement leads to an altered signal. Preferably, the contrast agent leads to a shortening of the T1 relaxation time and/or of the T2 relaxation time.

Preferably, the contrast agent is a hepatobiliary contrast agent such as, for example, Gd-EOB-DTPA or Gd-BOPTA.

In a particularly preferred embodiment, the contrast agent is a substance or a substance mixture with gadoxetic acid or a gadoxetic acid salt as contrast-enhancing active substance. Very particular preference is given to the disodium salt of gadoxetic acid (Gd-EOB-DTPA disodium).

The examination region is subjected to an MRI method and, in the course of this, MRI images are generated (measured) which show the examination region during the examination phase.

The measured MRI images can be present as two-dimensional images showing a sectional plane through the examination object. The measured MRI images can be present as a stack of two-dimensional images, with each individual image of the stack showing a different sectional plane. The measured MRI images can be present as three-dimensional images (3D images). In the interests of simpler illustration, the disclosure will be elucidated at some points in the present description on the basis of the presence of two-dimensional MRI images, without any wish, however, to restrict the disclosure to two-dimensional MRI images. It is clear to a person skilled in the art how it is possible to apply what is respectively described to stacks of two-dimensional images and to 3D images (see, in relation to this, for example M. Reisler, W. Semmler: *Magnetresonanztomographie* [Magnetic resonance imaging], Springer Verlag, 3rd edition, 2002, ISBN: 978-3-642-63076-7).

Usually, the measured MRI images are present as digital image files. The term "digital" means that the MRI images can be processed by a machine, generally a computer system. "Processing" is understood to mean the known methods for electronic data processing (EDP).

Digital image files can be present in various formats. For example, digital image files can be coded as raster graphics. Raster graphics consist of a grid arrangement of so-called picture elements (pixels) or volume element (voxel), to which a colour or a grey value is assigned in each case. The main features of a 2D raster graphic are therefore the image size (width and height measured in pixels, also informally called image resolution) and the colour depth. A colour is usually assigned to a picture element of a digital image file. The colour coding used for a picture element is defined, inter alia, in terms of the colour space and the colour depth. The simplest case is a binary image, in which a picture element stores a black-and-white value. In the case of an image, the colour of which is defined in terms of the so-called RGB colour space (RGB stands for the primary colours red, green and blue), each picture element consists of three subpixels, a subpixel for the colour red, a subpixel for the colour green and a subpixel for the colour blue. The colour of a picture element arises through the superimposition (additive blending) of the colour values of the subpixels. The colour value of a subpixel is divided for example into 256 colour nuances, which are called tonal values and usually range from 0 to 255. The colour nuance "0" of each colour channel is the darkest. If all three channels have the tonal value 0, the corresponding picture element appears black; if all three channels have the tonal value 255, the corresponding picture element appears white. When carrying out the present disclosure, digital image files (MRI images) are subjected to certain operations. In this connection, the operations affect predominantly the picture elements, or the tonal values of the individual picture elements. There is a multiplicity of possible digital image formats and colour codings. For simplification, it is assumed in this description that the present images are grey-scale raster graphics having a specific number of picture elements, with each picture element being assigned a tonal value indicating the grey value of the image. However, this assumption is not in any way to be understood as limiting. It is clear to a person skilled in the art of image processing how the teaching of said description can be applied to image files which are present in other image formats and/or in which the colour values are coded differently.

After the intravenous administration of a hepatobiliary contrast agent in the form of a bolus, the contrast agent reaches the liver first via the arteries. These are depicted with contrast enhancement in the corresponding MRI images. The phase in which the liver arteries are depicted with contrast enhancement in MRI images is referred to here as "arterial phase". Said phase starts immediately after the administration of the contrast agent and usually lasts 15 to 60 seconds.

Subsequently, the contrast agent reaches the liver via the liver veins. Whereas the contrast in the liver arteries is already decreasing, the contrast in the liver veins is reaching a maximum. The phase in which the liver veins are depicted with contrast enhancement in MRI images is referred to here as "venous phase". Said phase can already start during the arterial phase and overlap therewith. Usually, said phase starts 60 to 70 seconds after the intravenous administration and usually lasts 50 to 70 seconds.

Following the venous phase is the "late phase", in which the contrast in the liver arteries falls further and the contrast in the liver veins likewise falls and the contrast in the healthy liver cells gradually rises. Said phase usually starts 100 to 140 seconds after the administration of the contrast agent and usually lasts 50 to 70 seconds.

The arterial phase, the venous phase and the late phase are also referred to collectively as "dynamic phase".

10-20 minutes after its injection, a hepatobiliary contrast agent leads to a distinct signal enhancement in the healthy liver parenchyma. Said phase is referred to as "hepatobiliary phase". The contrast agent is eliminated only slowly from the liver cells; accordingly, the hepatobiliary phase can last for two hours and longer.

The stated phases are, for example, described in more detail in the following publications: J. Magn. Reson. Imaging, 2012, 35(3): 492-511, doi:10.1002/jmri.22833; Clujul Medical, 2015, Vol. 88 no. 4: 438-448, DOI: 10.15386/cjmed-414; Journal of Hepatology, 2019, Vol. 71: 534-542, (http://dx.doi.org/10.1016/j.jhep.2019.05.005).

In MRI images showing the examination region during the hepatobiliary phase, structures generated by blood vessels often cannot be distinguished from structures caused by liver lesions. Therefore, according to the disclosure, at least one MRI image of the liver or a portion of the liver of the examination object is (artificially) generated (calculated), in which the structures caused by the blood vessels are suppressed with respect to the surrounding healthy liver tissue, so that liver lesions are more easily identifiable.

This is done with the aid of at least one first MRI image and at least one second MRI image.

In this description, "first MRI image" refers to an MRI image in which blood vessels which are preferably depicted with contrast enhancement as a result of a contrast agent are identifiable. Preferably, the at least one first MRI image is at least one MRI image which was measured during the dynamic phase. Particular preference is given to at least one MRI image which was measured during the arterial phase and/or the venous phase. Very particular preference is given to one MRI image which was measured during the venous phase. It is also conceivable that at least two "first MRI images" are used, at least one which was measured in the arterial phase and at least one which was measured in the venous phase. Preferably, the at least one first MRI image is a T1-weighted depiction.

When using a paramagnetic contrast agent, the blood vessels are characterized by a high signal intensity in the at least one first MRI image owing to the contrast enhancement (high-signal depiction). Those (continuous) structures within a first MRI image that have a signal intensity within an empirically ascertainable range can thereby be assigned to blood vessels. This means that, with the at least one first MRI image, there is information about where blood vessels are depicted in the MRI images or which structures in the MRI images can be attributed to blood vessels (arteries and/or veins).

In this description, "second MRI image" refers to an MRI image showing the examination region during the hepatobiliary phase. During the hepatobiliary phase, the healthy liver tissue (parenchyma) is depicted with contrast enhancement. Those (continuous) structures within a second MRI image that have a signal intensity within an empirically ascertainable range can thus be assigned to healthy liver cells. Thus, the at least one second MRI image contains information as to where in the MRI images healthy liver cells are depicted or what structures in the MRI images can be attributed to healthy liver cells. Preferably, the at least one second MRI image is a T1-weighted depiction.

The information from the at least one first MRI image about the blood vessels is combined with the information from the at least one second MRI image about the healthy liver cells. What is (artificially) generated (calculated) in doing so is at least one third MRI image in which the difference in contrast between structures attributable to blood vessels and structures attributable to healthy liver cells is leveled out.

Here, the term "leveling out" means "equalizing" or "minimizing". The objective of leveling out is to make the boundaries between blood vessels and healthy liver cells disappear in the at least one third MRI image, and to make blood vessels and healthy liver cells appear in the at least one third MRI image as one uniform tissue, against which liver lesions stand out structurally owing to a different contrast.

Usually, one (number=1) first MRI image is combined with one (number=1) second MRI image to form one (number=1) third MRI image.

It is conceivable that, in addition to at least one first MRI image and at least one second MRI image, at least one native MRI image is also additionally used in order to calculate at least one third MRI image.

The third (artificial) MRI image can be generated in different ways.

In one embodiment (embodiment A) of the present disclosure, the generation of the at least one third MRI image comprises the following sub-steps:

identifying regions in the at least one first MRI image that depict blood vessels by identifying those pixels or voxels of the at least one first MRI image that have a tonal value within a first defined tonal-value band, and/or identifying regions in the at least one second MRI image that depict healthy liver cells by identifying those pixels or voxels of the at least one second MRI image that have a tonal value within a second defined tonal-value band, and at least partially superposing the at least one first MRI image and the at least one second MRI image and, in doing so, generating a third MRI image, the tonal values of the pixels or voxels having the tonal value within the first defined range and of the pixels or voxels having the tonal value within the second defined range being set to a common tonal value.

In a further embodiment (embodiment B) of the present disclosure, the generation of the third MRI image comprises the following sub-steps:

identifying blood vessels in the first MRI images by means of a segmentation method, identifying those structures in the second MRI images that correspond to the blood vessels in the first MRI images, identifying a (preferably arithmetically averaged) tonal value of healthy liver cells in the second MRI images, setting the tonal values of the structures in the second MRI images that correspond to the blood vessels in the first MRI images to the tonal value of healthy liver cells.

In a further embodiment (embodiment C) of the present disclosure, the generation of the third MRI image comprises the following sub-steps:

feeding the at least one first MRI image and the at least one second MRI image to a prediction model, the prediction model having been trained on the basis of reference MRI images by means of supervised learning to generate at least one third reference MRI image from at least one first reference MRI image and at least one second reference MRI image, the difference in contrast between structures attributable to blood vessels and structures attributable to healthy liver cells being leveled out in the at least one third reference MRI image, receiving at least one third MRI image, as output from the prediction model.

Embodiments A, B and C are more particularly elucidated further on in the description.

The (artificially) generated at least one third MRI image can be displayed on a monitor, be outputted on a printer and/or be stored in a data storage medium. Preferably, the at least one third MRI image is displayed on a monitor, with tonal values of the blood vessels and/or tonal values of the healthy liver cells being alterable such that their value is alterable from the value of the at least one first MRI image or the at least one second MRI image in a continuous manner in the direction of their value in the at least one third MRI image (e.g. by means of a (virtual) slide control). This embodiment has the advantage that a user can fade in and fade out between the individual MRI images and, in doing so, can for example fade in and fade out the structures indicating blood vessels in order to be able to identify lesions in the liver tissue.

The present disclosure provides a system which makes it possible to execute the method according to the disclosure.

The system comprises a receiving unit, a control and calculation unit and an output unit.

It is conceivable that the stated units are components of a single computer system; however, it is also conceivable that the stated units are components of multiple separate computer systems which are connected to one another via a network in order to transmit data and/or control signals from one unit to another unit.

A "computer system" is a system for electronic data processing that processes data by means of programmable calculation rules. Such a system usually comprises a "computer", that unit which comprises a processor for carrying out logical operations, and also peripherals.

In computer technology, "peripherals" refer to all devices which are connected to the computer and serve for the control of the computer and/or as input and output devices. Examples thereof are monitor (screen), printer, scanner, mouse, keyboard, drives, camera, microphone, loudspeaker, etc. Internal ports and expansion cards are, too, considered to be peripherals in computer technology.

Computer systems of today are frequently divided into desktop PCs, portable PCs, laptops, notebooks, netbooks and tablet PCs and so-called handhelds (e.g. smartphone); all these systems can be utilized for carrying out the disclosure.

Inputs into the computer system are achieved via input means such as, for example, a keyboard, a mouse, a microphone, a touch-sensitive display and/or the like.

The system according to the disclosure is configured to receive at least one first MRI image and at least one second MRI image and to combine these MRI images together to form at least one third MRI image.

The control and calculation unit serves for the control of the receiving unit, the coordination of the data and signal flows between various units, and the processing and generation of MRI images. It is conceivable that multiple control and calculation units are present.

The receiving unit serves for the receiving of MRI images. The MRI images can, for example, be transmitted from a magnetic resonance system (for example, via a network) or be read from a data storage medium. The magnetic resonance system can be a component of the system according to the disclosure. However, it is also conceivable that the system according to the disclosure is a component of a magnetic resonance system.

The at least one first MRI image and the at least one second MRI image and optionally further data are transmitted from the receiving unit to the control and calculation unit.

The control and calculation unit is configured to generate at least one third MRI image by combining the at least one first MRI image and the at least one second MRI image and leveling out the difference in contrast between blood vessels and healthy liver cells.

Via the output unit, the at least one third MRI image can be displayed (e.g. on a monitor), be outputted (e.g. via a printer) or be stored in a data storage medium.

The disclosure is more particularly elucidated below with reference to figures, without wishing to restrict the disclosure to the features or combinations of features that are shown in the figures, where:

FIG. 1 shows MRI images of a liver during the dynamic and hepatobiliary phase. In FIGS. 1($a$), 1($b$), 1($c$), 1($d$), 1($e$) and 1($f$), the same cross section through the liver at different time points is always depicted. The reference signs entered in FIGS. 1($a$), 1($b$), 1($d$) and 1($f$) apply to all of FIGS. 1($a$), 1($b$), 1($c$), 1($d$), 1($e$) and 1($f$); they are each entered only once merely for the sake of clarity.

FIG. 1($a$) shows the cross section through the liver (L) before the intravenous administration of a hepatobiliary contrast agent. At a time point between the time points depicted by FIGS. 1($a$) and 1($b$), a hepatobiliary contrast agent was administered intravenously (e.g. into a vein in the arm) as a bolus. This reaches the liver via the liver artery (A) in FIG. 1($b$). Accordingly, the liver artery is depicted with signal enhancement (arterial phase). A tumour (T), which is supplied with blood mainly via arteries, likewise stands out from the liver-cell tissue as a lighter (signal-enhanced) region. At the time point depicted in FIG. 1 ($c$), the contrast agent reaches the liver via the veins. In FIG. 1($d$), the venous blood vessels (V) stand out from the liver tissue as light (signal-enhanced) regions (portal-vein phase). At the same time, the signal intensity in the healthy liver cells, which are supplied with contrast agent mainly via the veins, continuously rises (FIG. 1($c$)→1($d$)→1($e$)→1($f$)). In the hepatobiliary phase depicted in FIG. 1($f$), the liver cells (P) are depicted with signal enhancement; the blood vessels and the tumour no longer have contrast agent and are accordingly depicted darkly; the blood vessels and the tumour are indistinguishable in the MRI image of FIG. 1($f$).

Figure 2:
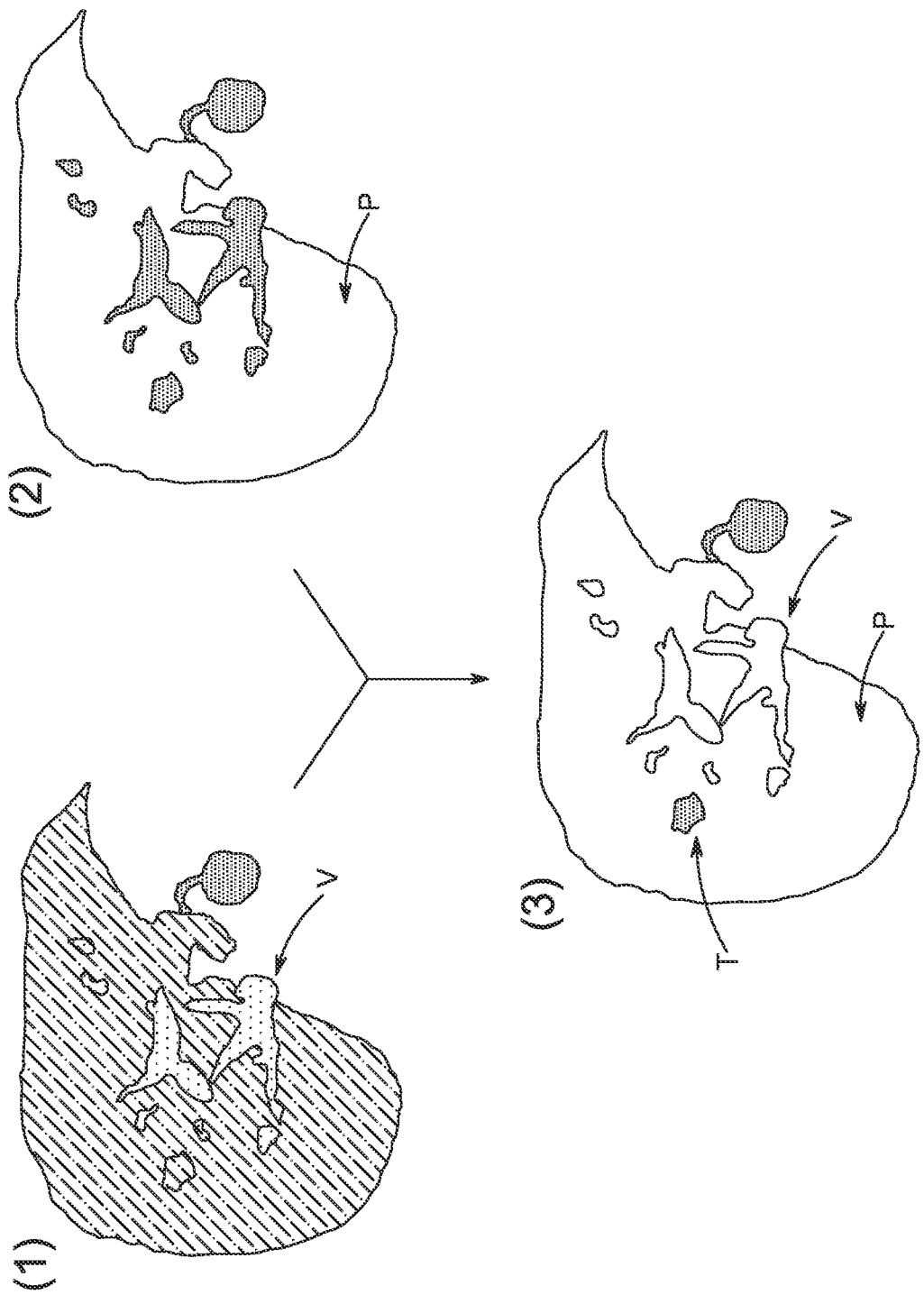
FIG. 2 shows exemplarily and schematically how a first MRI image and a second MRI image are combined in order to generate a third MRI image.

FIG. 2 shows exemplarily and schematically how a first MRI image (1) and a second MRI image (2) are combined together in order to generate a third MRI image (3). The first MRI image is the MRI image depicted in FIG. 1(d). In said image, the venous blood vessels (V) within the liver are easily identifiable. They have a high signal intensity owing to the contrast agent. The second MRI image is the MRI image depicted in FIG. 1(f). In said image, the healthy liver cells (P) are easily identifiable. They have a high signal intensity owing to the contrast agent. The first MRI image (1) and the second MRI image (2) are preferably measured MRI images. They are combined together to form the third MRI image (3). The third MRI image (3) is an artificially generated, i.e. calculated, MRI image. At the same time, regions within the MRI image (3) can absolutely contain measured values; however, the third MRI image has regions which are not measured, but instead, for example, the result of calculations. In the third MRI image (3), the contrast between the structures depicting blood tissue and the structures depicting liver cells is minimized, with the result that the tumour (T) is clearly identifiable.

Figure 3:
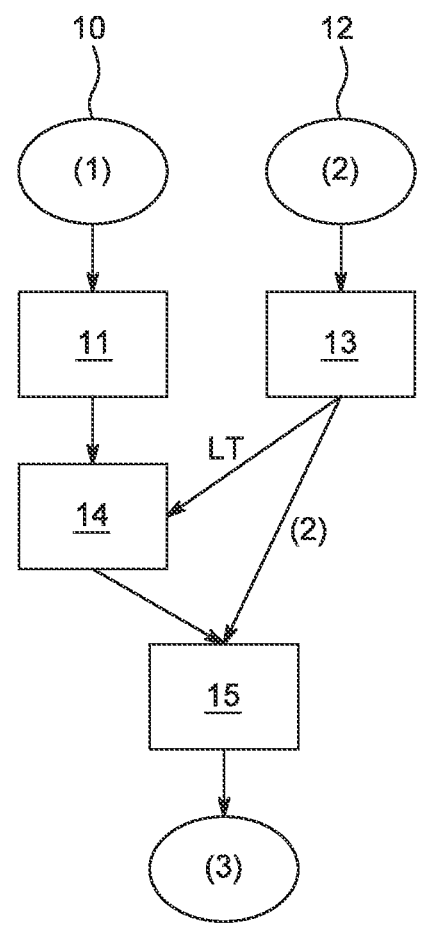
FIG. 3 shows exemplarily and schematically an embodiment of the computer-implemented method of the present disclosure in the form of a flow chart.
Figure 4:
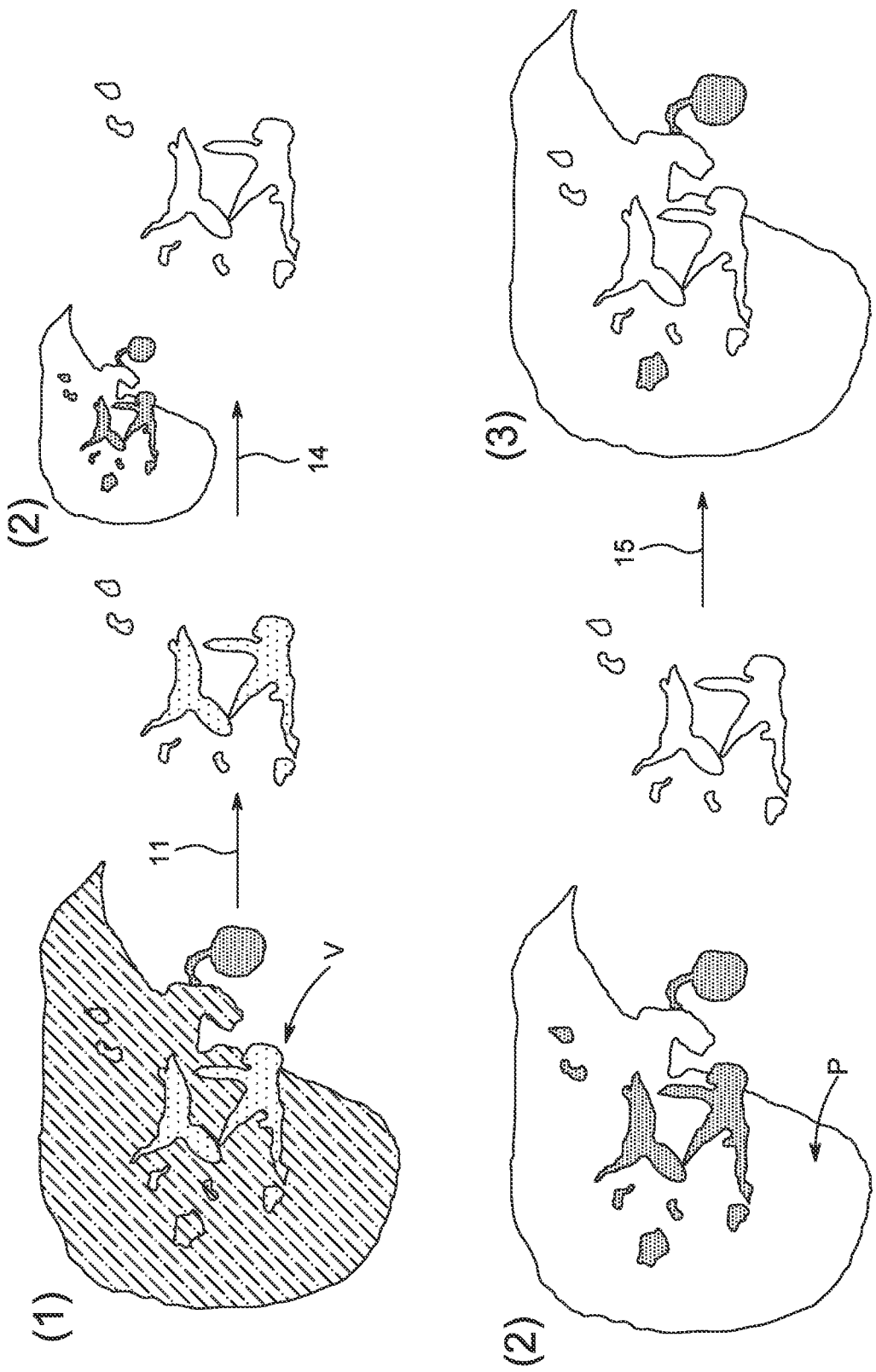
FIG. 4 shows exemplarily and schematically the embodiment of FIG. 3 based on MRI images.

FIG. 3 shows exemplarily and schematically one embodiment of the present disclosure in the form of a flow chart (embodiment A). The same embodiment is depicted in FIG. 4 on the basis of MRI images. This embodiment can be applied to individual two-dimensional MRI images (but is not restricted to such images).

In a first step (10), at least one first MRI image (1) is provided, the at least one first MRI image (1) showing a liver or a portion of a liver of an examination object, blood vessels in the liver being depicted with contrast enhancement (signal enhancement) as a result of a contrast agent. This can, for example, be the MRI image shown in FIG. 1(d).

The at least one first MRI image (1) displays venous blood vessels in a particularly light (signal-enhanced) manner in comparison with other tissue owing to the contrast agent present in the veins at the time point of measurement of the MRI image. Those regions within the at least one first MRI image that are depicted in a "particularly light" manner can thus be attributed to venous blood vessels.

In a further step (11), these regions depicted in a "particularly light" manner in the at least one first MRI image are identified. This is preferably done on the basis of the tonal values of the pixels or voxels of the regions. If the tonal value of a pixel or voxel is above a lower tonal-value threshold and below an upper tonal-value threshold, i.e. within a defined first tonal-value band, it can be assumed that the corresponding pixel or voxel depicts a portion of a venous blood vessel. The first tonal-value band (i.e. the lower and the upper tonal value) can be gained empirically. For example, a radiologist can specify in an MRI image the structures which can be attributed to blood vessels. The tonal values of said structures can then define the tonal-value band. In step (11), what are thus identified are those regions in the at least one first MRI image that have a tonal value within a defined (first) tonal-value band.

It is also conceivable that a native MRI image is subtracted from the at least one first MRI image (creation of a difference image). The difference image then merely shows the structures which are enhanced by contrast agent—and these are blood vessels in the case of the at least one first MRI image.

In a further step (12), at least one second MRI image (2) is provided, the at least one second MRI image showing the same liver or the same portion of the liver as the at least one first MRI image, the healthy liver tissue (parenchyma) being depicted with contrast enhancement as a result of a contrast agent. This can, for example, be the MRI image shown in FIG. 1(f).

In the at least one second MRI image, those regions depicting healthy liver cells can be identified. This can be done analogously to the procedure in step (11), i.e. what are identified are those pixels or voxels in the at least one second MRI image, the tonal value of which is above a lower tonal-value threshold and below an upper tonal-value threshold, i.e. within a defined second tonal-value band. The second tonal-value band (i.e. the lower and the upper tonal value) can likewise be gained empirically.

Similarly, it is also possible here to again create a difference image (second MRI image minus native image). Here, the difference image also merely shows the structures which are enhanced by contrast agent—and these are healthy liver cells in the case of the at least one second MRI image.

In a further step (13), a tonal value is ascertained. Said tonal value is also referred to here as the liver tonal (LT) value. This can, for example, be the arithmetically averaged tonal value of those pixels or voxels which depict healthy liver tissue in the at least one second MRI image.

In a further step (14), the tonal values of the pixels or voxels depicting venous blood vessels in the at least one first MRI image are set to the liver tonal value.

It is also conceivable that, in addition, the tonal values of the pixels or voxels depicting healthy liver cells in the at least one second MRI image are set to the (averaged) liver tonal value.

In a further step (15), the at least one first MRI image and the at least one second MRI image are at least partially superposed. "Superposing" or else "superimposing" refers to the combination of the at least one first MRI image and of the at least one second MRI image to form at least one third MRI image. Superposing is usually carried out for a pair of a first MRI image and a second MRI image in a pixel-by-pixel or voxel-by-voxel manner. If the examination object did not move during the acquisition of the first and the second MRI image, a pixel or a voxel of the first MRI image corresponds exactly to a pixel or voxel of the second MRI image: the corresponding pixels or voxels show the same examination region at different time points. To generate the third MRI image, some pixels or voxels of the first MRI image can be used as pixels or voxels of the third MRI image and some pixels or voxels of the second MRI image can be used as pixels or voxels of the third MRI image. It is similarly conceivable that the tonal values of some pixels or voxels of the first MRI image are linked mathematically to the corresponding pixels or voxels of the second MRI image: for example, (standardized) cumulative or difference images can be generated. What is crucial is that the difference in contrast between regions attributable to blood vessels and regions attributable to healthy liver cells is leveled out in the third MRI image. This can be done by setting the tonal values of those pixels or voxels attributable to blood vessels and the tonal values of those pixels or voxels attributable to healthy liver cells to the same tonal value, for example to the average liver tonal value, in the third MRI image. If the examination object has moved between the measurement of the first MRI image and the measurement of the second MRI image, a movement correction must be performed before the MRI images are superposed. Movement correction methods are described in the prior art (see, for example: EP3118644, EP3322997, US20080317315, US20170269182, US20140062481, EP2626718).

Figure 5:
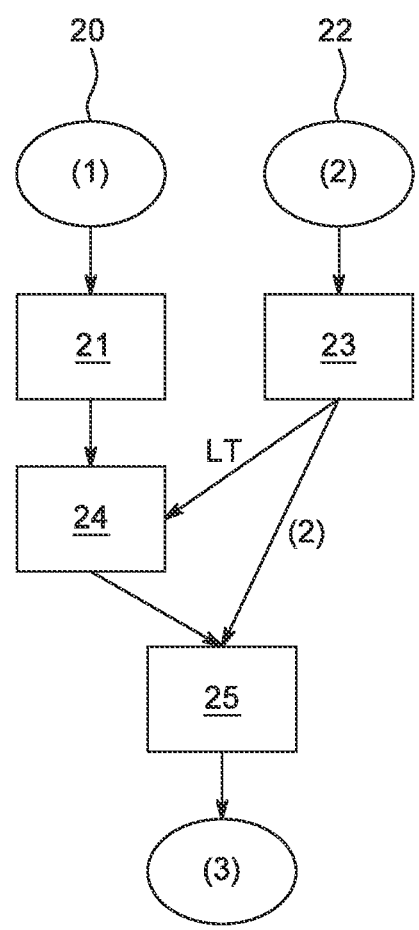
FIG. 5 shows exemplarily and schematically a further embodiment of the computer-implemented method of the present disclosure in the form of a flow chart.

FIG. 5 shows exemplarily and schematically a further embodiment of the present disclosure in the form of a flow chart (embodiment B).

In a first step (20), a first three-dimensional MRI image (1) is provided, the at least one first three-dimensional MRI image showing a liver or a portion of a liver of an examination object, blood vessels in the liver being depicted with contrast enhancement as a result of a contrast agent.

In a further step (21), the blood vessels in the first three-dimensional MRI image are identified with the aid of a segmentation method. In the first three-dimensional MRI image, blood vessels are characterized by the fact that they are depicted with contrast enhancement owing to the contrast agent, i.e. have a tonal value within a defined first tonal-value band.

Segmentation methods are widely described in the literature. The following publications are cited as examples: F. Conversano et al.: *Hepatic Vessel Segmentation for 3D Planning of Liver Surgery*, Acad Radiol 2011, 18:461-470; S. Moccia et al.: Blood vessel segmentation algorithms Review of methods, datasets and evaluation metrics, Computer Methods and Programs in Biomedicine 158 (2018) 71-91; M. Marcan et al.: Segmentation of hepatic vessels from MRI images for planning of electroporation-based treatments in the liver, Radiol Oncol 2014; 48 (3): 267-281; T. A. Hope et al.: *Improvement of Gadoxetate Arterial Phase Capture With a High Spatio-Temporal Resolution Multiphase Three-Dimensional SPGR-Dixon Sequence*, Journal of Magnetic Resonance Imaging 38:938-945 (2013); WO2009/135923A1, U.S. Pat. No. 6,754,376B1, WO2014/162273A1, WO2017/139110A1, WO2007/053676A2, EP2750102A1.

In a further step (22), a second three-dimensional MRI image (2) is provided, the second three-dimensional MRI image showing the same liver or the same portion of the liver as the first three-dimensional MRI image, the healthy liver tissue (parenchyma) being depicted with contrast enhancement as a result of a contrast agent.

In a further step (23), a tonal value is ascertained. Said tonal value is also referred to here as the liver tonal (LT) value. This can, for example, be the arithmetically averaged tonal value of those voxels depicting healthy liver tissue in the second three-dimensional MRI image.

In a further step (24), the tonal values of the voxels depicting the segmented blood vessels in the first three-dimensional MRI image are set to the liver tonal value.

It is conceivable that the tonal values of the voxels depicting healthy liver cells in the second three-dimensional MRI image are also set to the (averaged) liver tonal value.

In a further step (25), the first three-dimensional MRI image and the second three-dimensional MRI image are combined together to form a third three-dimensional MRI image. To this end, the blood vessels segmented from the first three-dimensional MRI image and having the liver tonal value are introduced into the second three-dimensional MRI image, where the respective voxels of the first three-dimensional MRI image replace the corresponding voxels of the second three-dimensional MRI image. If necessary, a movement correction must be performed. Since the voxels representing blood vessels are set to the liver tonal value, the difference in contrast between the regions of the third MRI image that depict blood vessels and the regions of the third MRI image that depict healthy liver cells is leveled out.

Figure 6:
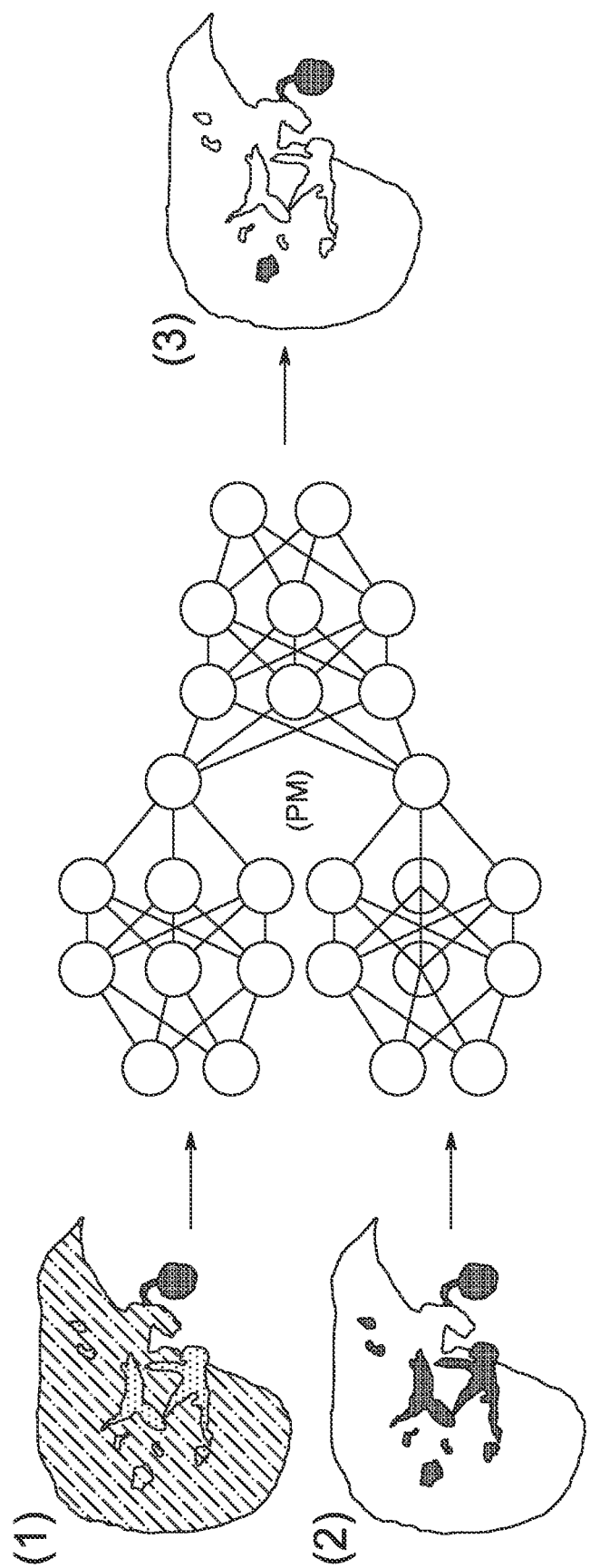
FIG. 6 shows exemplarily and schematically the embodiment of FIG. 5 based on MRI images.

FIG. 6 shows exemplarily and schematically a further embodiment of the present disclosure (embodiment C). A first MRI image (1) is provided, the first MRI image showing a liver or a portion of a liver of an examination object, blood vessels in the liver being depicted with contrast enhancement (signal enhancement) as a result of a contrast agent.

A second MRI image (2) is provided, the second MRI image showing the same liver or the same portion of the liver as the first MRI image, the healthy liver tissue (parenchyma) being depicted with contrast enhancement (signal enhancement) as a result of a contrast agent.

The first MRI image (1) and the second MRI image (2) are fed to a prediction model (PM).

The prediction model (PM) is configured to generate, on the basis of the first MRI image (1) and the second MRI image (2), a third MRI image (3), wherein the difference in contrast between structures attributable to blood vessels and structures attributable to healthy liver cells is leveled out in the third MRI image.

The prediction model was preferably created with the aid of a self-learning algorithm in a supervised machine learning process with a training data set. The training data set comprises a multiplicity of first MRI images, second MRI images and the associated third MRI images, wherein each third MRI image is a combination of a first and a second MRI image, wherein the difference in contrast between structures attributable to blood vessels and structures attributable to healthy liver cells is leveled out in the third MRI image. The training data set can be generated, for example, with the aid of embodiments A and/or B of the present disclosure. In this description, the training data are also referred to as reference MRI images. A first reference MRI image is accordingly an MRI image which shows a liver or a portion of a liver of an examination object, blood vessels in the liver being depicted with contrast enhancement as a result of a contrast agent; a second reference MRI image is accordingly an MRI image which shows the same liver or the same portion of the liver as the first reference MRI image, the healthy liver tissue (parenchyma) being depicted with contrast enhancement as a result of a contrast agent; a third reference MRI image is accordingly a combination according to the disclosure of a first and a second reference MRI image, in which the difference in contrast between structures which can be attributed to blood vessels and structures which can be attributed to healthy liver cells has been leveled out.

The self-learning algorithm generates, during machine learning, a statistical model which is based on the training data. This means that the examples are not simply learnt by heart, but that the algorithm "recognizes" patterns and regularities in the training data. The algorithm can thus also assess unknown data. Validation data can be used to test the quality of the assessment of unknown data.

The self-learning algorithm is trained by means of supervised learning, i.e. first and second reference MRI images are presented to the algorithm and it is informed of which third reference MRI images are associated with the particular first and second reference MRI images. The algorithm then learns a relationship between the reference MRI images in order to predict (to calculate) third MRI images for unknown first and second MRI images.

Self-learning algorithms trained by means of supervised learning are widely described in the prior art (see, for example, C. Perez: Machine Learning Techniques: Supervised Learning and Classification, Amazon Digital Services LLC—Kdp Print Us, 2019, ISBN 1096996545, 9781096996545, WO2018/183044A1, WO2018/200493, WO2019/074938A1, WO2019/204406A1, WO2019/241659A1).

Preferably, the prediction model is an artificial neural network.

Such an artificial neural network comprises at least three layers of processing elements: a first layer with input neurons (nodes), an N-th layer with at least one output neuron (nodes) and N−2 inner layers, where N is a natural number and greater than 2.

The input neurons serve to receive digital MRI images as input values. Normally, there is one input neuron for each pixel or voxel of a digital MRI image. There can be additional input neurons for additional input values (e.g. information about the examination region, about the examination object and/or about conditions which prevailed when generating the MRI images).

In such a network, the output neurons serve as a third MRI image for a first and a second MRI image.

The processing elements of the layers between the input neurons and the output neurons are connected to one another in a predetermined pattern with predetermined connection weights.

Preferably, the artificial neural network is a so-called convolutional neural network (CNN for short).

A convolutional neural network is capable of processing input data in the form of a matrix. This makes it possible to use digital MRI images depicted as a matrix (e.g. width× height×colour channels) as input data. By contrast, a normal neural network, for example in the form of a multilayer perceptron (MLP), requires a vector as input, i.e. to use an MRI image as input, the pixels or voxels of the MRI image would have to be rolled out successively in a long chain. As a result, normal neural networks are, for example, not capable of recognizing objects in an MRI image independently of the position of the object in the MRI image. The same object at a different position in the MRI image would have a completely different input vector.

A CNN consists essentially of filters (convolutional layer) and aggregation layers (pooling layer) which are repeated alternately and, at the end, of one layer or multiple layers of "normal" completely connected neurons (dense/fully connected layer).

Details can be gathered from the prior art (see, for example: S. Khan et al.: A Guide to Convolutional Neural Networks for Computer Vision, Morgan & Claypool Publishers 2018, ISBN 1681730227, 9781681730226).

The training of the neural network can, for example, be carried out by means of a backpropagation method. In this connection, what is striven for, for the network, is a mapping of given input vectors onto given output vectors that is as reliable as possible. The mapping quality is described by an error function. The goal is to minimize the error function. In the case of the backpropagation method, an artificial neural network is taught by altering the connection weights.

In the trained state, the connection weights between the processing elements contain information regarding the relationship between the first and second reference MRI images and the third reference MRI images that can be used in order to predict one or more third MRI images on the basis of new first and second MRI images.

A cross-validation method can be used in order to divide the data into training and validation data sets. The training data set is used in the backpropagation training of network weights. The validation data set is used in order to check the accuracy of prediction with which the trained network can be applied to unknown MRI images.

Figure 7:
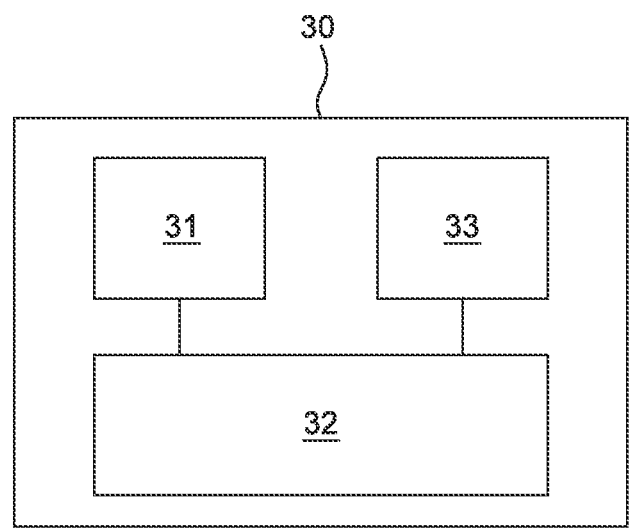
FIG. 7 shows schematically an embodiment of the system of the present disclosure.

FIG. 7 shows schematically a preferred embodiment of the system according to the disclosure. The system (30) comprises a receiving unit (31), a control and calculation unit (32) and an output unit (33).

The control and calculation unit (32) is configured to prompt the receiving unit (31) to receive at least one first MRI image of an examination object, the at least one first MRI image showing a liver or a portion of a liver of the examination object, blood vessels in the liver being depicted with contrast enhancement as a result of a contrast agent.

The control and calculation unit (32) is further configured to prompt the receiving unit (31) to receive at least one second MRI image of an examination object, the at least one second MRI image showing the same liver or the same portion of the liver, healthy liver cells being depicted with contrast enhancement as a result of a contrast agent.

The control and calculation unit (32) is further configured to generate at least one third MRI image by combining the at least one first MRI image and the at least one second MRI image and leveling out the difference in contrast between blood vessels and healthy liver cells.

The control and calculation unit (32) is further configured to prompt the output unit to display the at least one third MRI image, to output it or to store it in a data storage medium.

Figure 8:
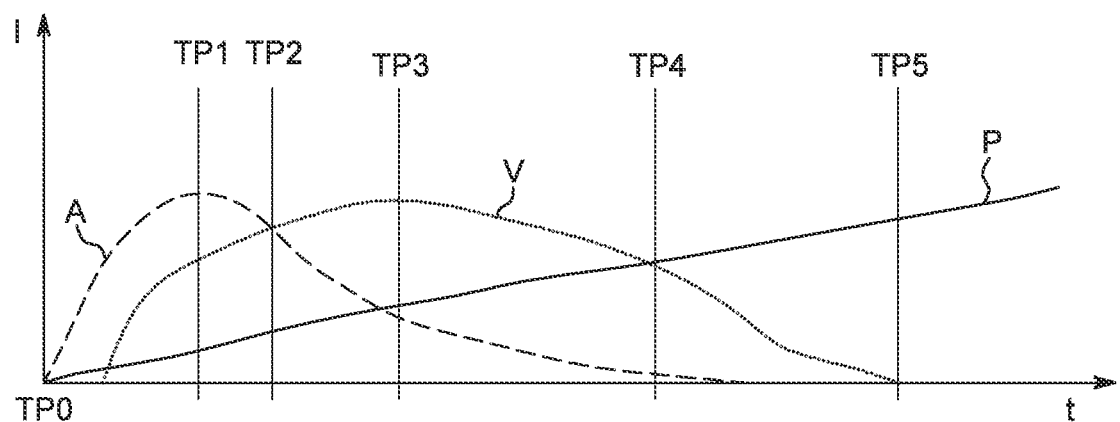

FIG. 8 shows schematically the temporal profile of the concentrations of contrast agent in the liver arteries (A), the liver veins (V) and the healthy liver cells (P) after an intravenous administration of a hepatobiliary contrast agent as a bolus. The concentrations are depicted in the form of the signal intensities I in the stated areas (liver arteries, liver veins, liver cells) in the magnetic resonance measurement as a function of the time t. Upon an intravenous bolus injection, the concentration of the contrast agent rises in the liver arteries (A) first of all (dashed curve). The concentration passes through a maximum and then drops. The concentration in the liver veins (V) rises more slowly than in the liver arteries and reaches its maximum later (dotted curve). The concentration of the contrast agent in the healthy liver cells (P) rises slowly (continuous curve) and reaches its maximum only at a very much later time point (the maximum is not depicted in FIG. 8). A few characteristic time points can be defined: At time point TP0, contrast agent is administered intravenously as a bolus. At time point TP1, the concentration (the signal intensity) of the contrast agent in the liver arteries reaches its maximum. At time point TP2, the curves of the signal intensities for the liver arteries and the liver veins intersect. At time point TP3, the concentration (the signal intensity) of the contrast agent in the liver veins passes through its maximum. At time point TP4, the curves of the signal intensities for the liver arteries and the liver cells intersect. At time point T5, the concentrations in the liver arteries and the liver veins have dropped to a level at which they no longer cause a measurable contrast enhancement.

In a preferred embodiment, the at least one first MRI image is an MRI image which has been generated in the time span between TP0 and TP5, preferably between TP0 and TP4. In a preferred embodiment, at least two first MRI images are used to calculate the at least one third MRI image, preferably an MRI image which has been generated in the time span between TP0 and TP3 and a further MRI image which has been generated in the time span between TP2 and TP4.

In a preferred embodiment, the at least one second MRI image is an MRI image which has been generated after TP5.

The invention claimed is:

1. A computer-implemented method comprising:
receiving at least one first Magnetic Resonance Imaging ("MRI") image of an examination object, the at least one first MRI image showing a liver or a portion of a liver of the examination object, blood vessels in the liver being depicted with contrast enhancement as a result of a contrast agent,
receiving at least one second MRI image of the examination object, the at least one second MRI image showing the liver or the portion of the liver, healthy liver cells being depicted with contrast enhancement as a result of the contrast agent,
generating at least one third MRI image by combining the at least one first MRI image with the at least one second MRI image and levelling out the difference in contrast between the blood vessels and the healthy liver cells and,
displaying and/or outputting the at least one third MRI image and/or storing the at least one third MRI image in a data storage medium.

2. The method of claim 1, wherein the at least one first MRI image is a T1-weighted depiction of the liver or the portion of the liver in a venous phase after administration of a hepatobiliary, paramagnetic contrast agent, wherein T1 is a longitudinal or spin-lattice relaxation time required to reach 63.21% of equilibrium magnetization prior to resonance excitation.

3. The method of claim 1, wherein the at least one second MRI image is a T1-weighted depiction of the liver or the portion of the liver in a hepatobiliary phase after administration of a hepatobiliary, paramagnetic contrast agent, wherein T1 is a longitudinal or spin-lattice relaxation time required to reach 63.21% of equilibrium magnetization prior to resonance excitation.

4. The method of claim 1, wherein the contrast agent is a substance or a substance mixture with gadoxetic acid or a gadoxetic acid salt as contrast-enhancing active substance.

5. The method of claim 1, wherein generating the at least one third MRI image further comprises:
identifying regions in the at least one first MRI image that depict blood vessels by identifying those pixels or voxels of the at least one first MRI image that have a tonal value within a first defined tonal-value band, and/or
identifying regions in the at least one second MRI image that depict healthy liver cells by identifying those pixels or voxels of the at least one second MRI image that have a tonal value within a second defined tonal-value band, and
at least partially superposing the at least one first MRI image and the at least one second MRI image and, in doing so, generating the at least one third MRI image, the tonal values of the pixels or voxels having the tonal value within the first defined range and of the pixels or voxels having the tonal value within the second defined range being set to a common tonal value in the at least one third MRI image.

6. The method of claim 1, wherein generating the at least one third MRI image further comprises:
identifying the blood vessels in the at least one first MRI image by means of a segmentation method,
identifying those structures in the at least one second MRI image that correspond to the blood vessels in the at least one first MRI image,
identifying a tonal value of healthy liver cells in the at least one second MRI image and,
setting the tonal values of the structures in the at least one second MRI image that correspond to the blood vessels in the at least one first MRI image to the tonal value of healthy liver cells.

7. The method of claim 1, wherein generating the at least one third MRI image further comprises:
feeding the at least one first MRI image and the at least one second MRI image to a prediction model, the prediction model having been trained by means of supervised learning based on reference MRI images to generate at least one third reference MRI image from at least one first reference MRI image and at least one second reference MRI image, the difference in contrast between structures attributable to blood vessels and structures attributable to healthy liver cells being levelled out in the at least one third reference MRI image,
receiving the at least one third MRI image, as output from the prediction model.

8. The method of claim 7, wherein the prediction model is an artificial neural network.

9. The method of claim 1, wherein the contrast agent comprises gadolinium ethoxybenzyl diethylenetriaminepentaacetic diethylenetriamine pentaacetic acid ("Gd-EOB-DTPA") disodium.

10. A computer program product comprising a computer program loaded into a memory of a computer system, where it prompts the computer system to execute the following:
receiving at least one first Magnetic Resonance Imaging ("MRI") image of an examination object, the at least one first MRI image showing a liver or a portion of a liver of the examination object, blood vessels in the liver being depicted with contrast enhancement as a result of a contrast agent,
receiving at least one second MRI image of the examination object, the at least one second MRI image showing the liver or the portion of the liver, healthy liver cells being depicted with contrast enhancement as a result of the contrast agent,
generating at least one third MRI image by combining the at least one first MRI image with the at least one second MRI image and levelling out the difference in contrast between the blood vessels and the healthy liver cells and,
displaying and/or outputting the at least one third MRI image and/or storing the at least one third MRI image in a data storage medium.

11. The computer program product of claim 10, wherein generating the at least one third MRI image further comprises:
identifying regions in the at least one first MRI image that depict blood vessels by identifying those pixels or voxels of the at least one first MRI image that have a tonal value within a first defined tonal-value band, and/or
identifying regions in the at least one second MRI image that depict healthy liver cells by identifying those pixels or voxels of the at least one second MRI image that have a tonal value within a second defined tonal-value band, and
at least partially superposing the at least one first MRI image and the at least one second MRI image and, in doing so, generating the at least one third MRI image, the tonal values of the pixels or voxels having the tonal value within the first defined range and of the pixels or voxels having the tonal value within the second defined range being set to a common tonal value in the at least one third MRI image.

12. The computer program product of claim 10, wherein generating the at least one third MRI image further comprises:
identifying the blood vessels in the at least one first MRI image by means of a segmentation method,
identifying those structures in the at least one second MRI image that correspond to the blood vessels in the at least one first MRI image,
identifying a tonal value of healthy liver cells in the at least one second MRI image and,
setting the tonal values of the structures in the at least one second MRI image that correspond to the blood vessels in the at least one first MRI image to the tonal value of healthy liver cells.

13. The computer program product of claim 10, wherein generating the at least one third MRI image further comprises:
feeding the at least one first MRI image and the at least one second MRI image to a prediction model, the prediction model having been trained by means of supervised learning based on reference MRI images to generate at least one third reference MRI image from at least one first reference MRI image and at least one second reference MRI image, the difference in contrast between structures attributable to blood vessels and structures attributable to healthy liver cells being levelled out in the at least one third reference MRI image and,
receiving the at least one third MRI image, as output from the prediction model.

14. The computer program product of claim 10, wherein the prediction model is an artificial neural network.

15. Use of a contrast agent in an Magnetic Resonance Imaging ("MRI") method, the MRI method comprising:
administering the contrast agent, the contrast agent spreading in a liver of an examination object,
generating at least one first MRI image, the at least one first MRI image showing the liver or a portion of the liver of the examination object, blood vessels in the liver being depicted with contrast enhancement as a result of the contrast agent,
generating at least one second MRI image, the at least one second MRI image showing the liver or the portion of the liver, healthy liver cells being depicted with contrast enhancement as a result of the contrast agent,
generating at least one third MRI image by combining the at least one first MRI image with the at least one second MRI image and levelling out the difference in contrast between the blood vessels and the healthy liver cells, and
displaying and/or outputting the at least one third MRI image and/or storing the at least one third MRI image in a data storage medium.

16. The use of a contrast agent in the MRI method of claim 15, wherein the contrast agent is a substance or a substance mixture with gadoxetic acid or a gadoxetic acid salt as contrast-enhancing active substance.

17. The use of a contrast agent in the Magnetic Resonance Imaging ("MRI") method of claim 15, wherein the contrast agent comprises Gd-EOB-DTPA gadolinium ethoxybenzyl diethylenetriaminepentaacetic diethylenetriamine pentaacetic acid ("Gd-EOB-DTPA") disodium.

* * * * *